US006926762B2

(12) United States Patent
Kim et al.

(10) Patent No.: US 6,926,762 B2
(45) Date of Patent: Aug. 9, 2005

(54) AIR CLEANING APPARATUS

(75) Inventors: Seung-Chul Kim, Seoul (KR); Jai-Kwon Lee, Suwon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 128 days.

(21) Appl. No.: 10/673,187

(22) Filed: Sep. 30, 2003

(65) Prior Publication Data
US 2004/0118288 A1 Jun. 24, 2004

(30) Foreign Application Priority Data
Dec. 23, 2002 (KR) .............................. 10-2002-0082702

(51) Int. Cl.[7] .............................................. B01D 35/30
(52) U.S. Cl. ........................... 96/397; 96/417; 96/423; 55/343; 55/350.1; 55/470; 55/471; 55/472; 55/484
(58) Field of Search ...................... 96/397, 417, 423; 55/342, 343, 350.1, 467, 470, 471, 472, 484; 95/8

(56) References Cited

U.S. PATENT DOCUMENTS 6,050,774 A * 4/2000 LeBaron ................. 415/121.2
6,361,590 B1  3/2002 Gilbert, Jr. et al.

FOREIGN PATENT DOCUMENTS

| JP | 63044920 A | * 2/1988 | ............. 73/863.23 |
| JP | 2000-152983 | 6/2000 | |
| WO | WO 2004/108248 A2 | * 12/2004 | |

* cited by examiner

Primary Examiner—Robert A. Hopkins
(74) Attorney, Agent, or Firm—Staas & Halsey LLP

(57) ABSTRACT

An air cleaning apparatus includes an air cleaning unit at its upper and lower portions thereof which are independently operated to effectively and uniformly clean room air in a short period of time. The air cleaning apparatus includes a cabinet provided with first and second air cleaning units. The first and second air cleaning units are connected to each other, and are provided with a blowing unit and a filtering unit. First and second sensors are provided on the cabinet in such a way as to be spaced apart from each other, and to sense air pollution levels at opposite sides of a room. The air cleaning apparatus also includes a control unit. The control unit controls the first and second air cleaning units so that both the first and second air cleaning units are operated or either of the first and second air cleaning units is operated, according to data obtained from first and second sensors.

17 Claims, 4 Drawing Sheets

AIR CLEANING APPARATUS

CROSS-REFERENCE TO RELATED APPLICATIONS

This application claims the benefit of Korean Application No. 2002-82702, filed Dec. 23, 2002, in the Korean Intellectual Property Office, the disclosure of which is incorporated herein by reference.

BACKGROUND OF THE INVENTION

1. Field of the Invention

The present invention relates, in general, to air cleaning apparatuses and, more particularly, to an air cleaning apparatus with a plurality of air cleaning units which are independently operated.

2. Description of the Related Art

As is well known to those skilled in the art, an air cleaning apparatus is an appliance which removes dust or bacteria from air to clean the air. The air cleaning apparatus is provided with a blowing unit and a filtering unit. The blowing unit functions to suck room air and forcibly circulate the room air. The filtering unit functions to remove the dust or bacteria from the air which is circulated by the blowing unit.

The air cleaning apparatus includes a cabinet which defines an external appearance of the air cleaning apparatus. The blowing unit includes a blowing fan provided in the cabinet, and a motor to drive the blowing fan. The filtering unit is provided at an air inlet side or an air outlet side of the cabinet, and includes a free filter of a net structure with relatively large meshes, a fine dust filter which is made of polypropylene resin or polyethylene resin to have the shape of a non-woven fabric, etc. The filters are arranged to be superposed.

The air cleaning apparatus having a construction as described above is operated as follows. While the room air is circulated by an operation of the blowing unit, the air passes through the filtering unit. At this time, impurities such as the dust are removed from the air, thus cleaning the room air.

The air cleaning apparatus is installed at a position inside a room to clean the room air. When the conventional air cleaning apparatus is operated to clean the room air, the room air around the air cleaning apparatus is smoothly circulated, thus accomplishing an excellent air cleaning effect. However, an air cleaning effect is relatively poor in areas of the room distant from the air cleaning apparatus, so it takes a considerably long time to uniformly and completely clean the room air.

SUMMARY OF THE INVENTION

Accordingly, it is an aspect of the present invention to provide an air cleaning apparatus provided with a plurality of air cleaning units which are connected to each other and are separately or simultaneously operated, thus allowing room air to be effectively cleaned in a short period of time.

Additional aspects and advantages of the invention will be set forth in part in the description which follows and, in part, will be obvious from the description, or may be learned by practice of the invention.

The foregoing and/or other aspects of the present invention are achieved by providing an air cleaning apparatus, including a cabinet provided with first and second air cleaning units, first and second sensors, and a control unit. The first and second air cleaning units are connected to each other, and each are provided with a blowing unit and a filtering unit. First and second sensors are provided on the cabinet to be spaced apart from each other, and sense air pollution levels at opposite sides of a room. The control unit controls the first and second air cleaning units so that both the first and second air cleaning units are operated or either of the first and second air cleaning units is operated, according to data obtained from the first and second sensors.

According to an aspect of the invention, the air cleaning units each are provided with an air inlet port and an air outlet port so that air is circulated through the air cleaning units, the blowing unit is installed in each of the air cleaning units, and the filtering unit is removably mounted to the air inlet port of each of the air cleaning units.

According to an aspect of the invention, the blowing unit includes a blowing fan installed in each of the air cleaning units, and a motor installed in each of the air cleaning units to rotate the blowing fan.

According to an aspect of the invention, the motor includes a variable speed motor which is controllable via a rotating speed thereof.

According to another aspect of the invention, the filtering unit includes a filter casing removably mounted to the air inlet port of each of the air cleaning units, and at least one filter mounted to the filter casing.

According to an aspect of the invention, the filter, mounted to the filter casing, includes an antibacterial free filter, an electrostatic dust filter, and a fine dust filter which are arranged to be superposed.

According to an aspect of the invention, the air cleaning apparatus further includes a control panel mounted to a predetermined portion of the cabinet, and provided with a plurality of control buttons to control an operation of the air cleaning apparatus and a display to display an operating state of the air cleaning apparatus.

According to an aspect of the invention, the first and second air cleaning units are provided at upper and lower portions of the cabinet, respectively, and the first and second sensors are mounted to the upper and lower portions of the cabinet, respectively.

According to an aspect of the invention, the first and second air cleaning units are provided at both sides of the cabinet, and the first and second sensors are mounted to both ends of the cabinet.

BRIEF DESCRIPTION OF THE DRAWINGS

The above and/or other aspects and advantages of the invention will become apparent and more readily appreciated from the following description of the preferred embodiments, taken in conjunction with the accompanying drawings of which.

DETAILED DESCRIPTION OF THE PREFERRED EMBODIMENTS

Figure 1:
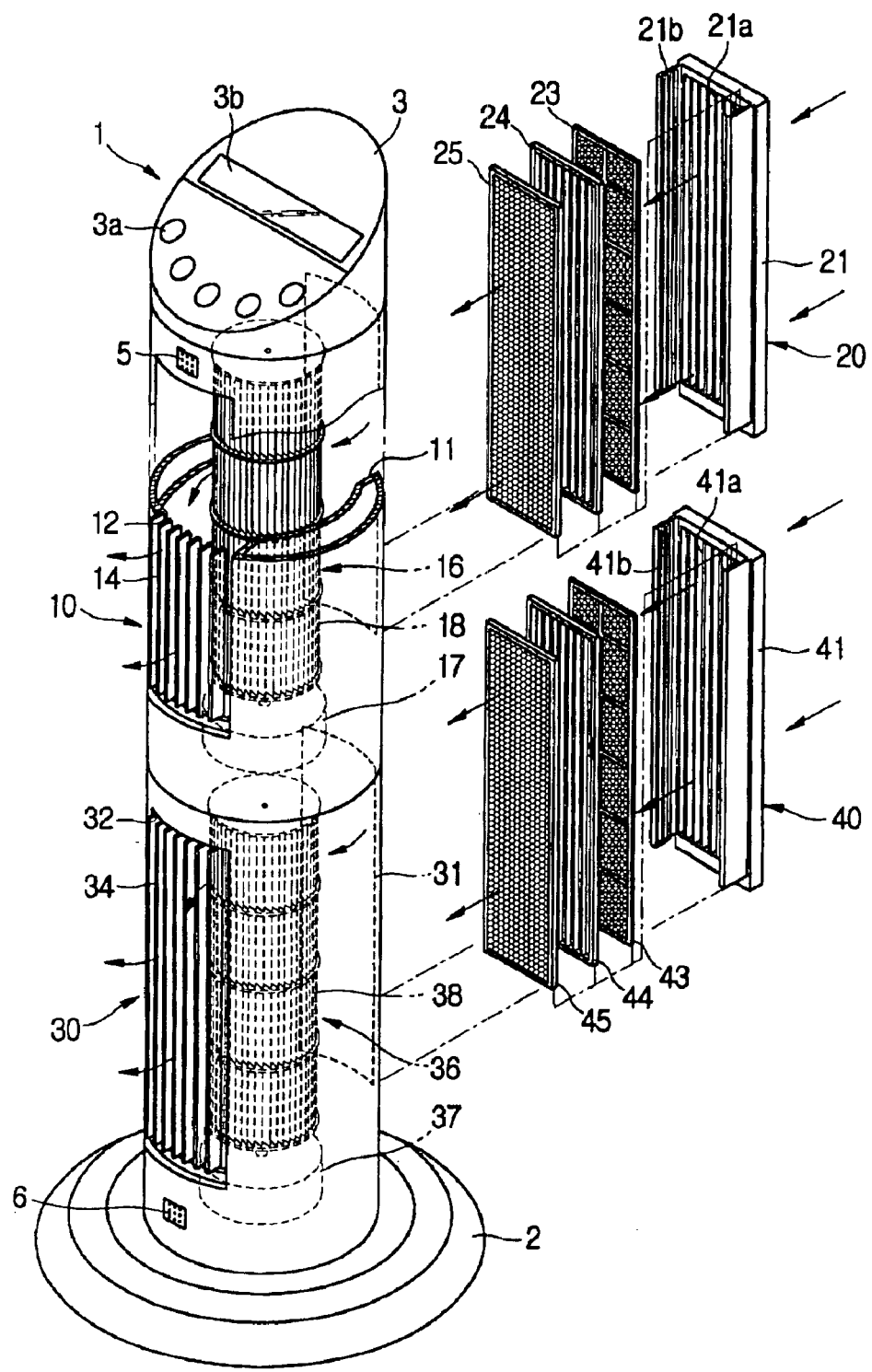
FIG. 1 is a perspective view illustrating an air cleaning apparatus, according to an embodiment of the present invention.

Reference will now be made in detail to the present preferred embodiments of the present invention, examples of which are illustrated in the accompanying drawings, wherein like reference numerals refer to like elements throughout.

Figure 2:
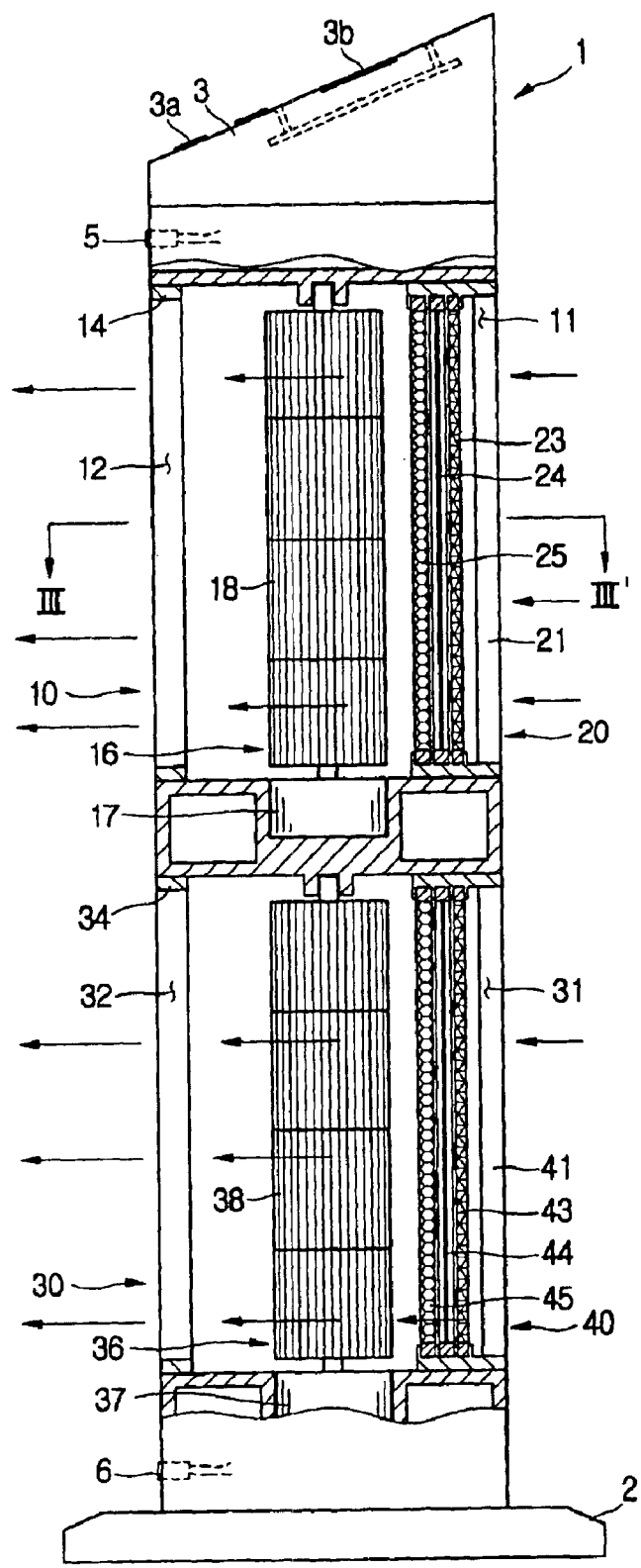
FIG. 2 is a sectional view of the air cleaning apparatus of FIG. 1.
Figure 3:
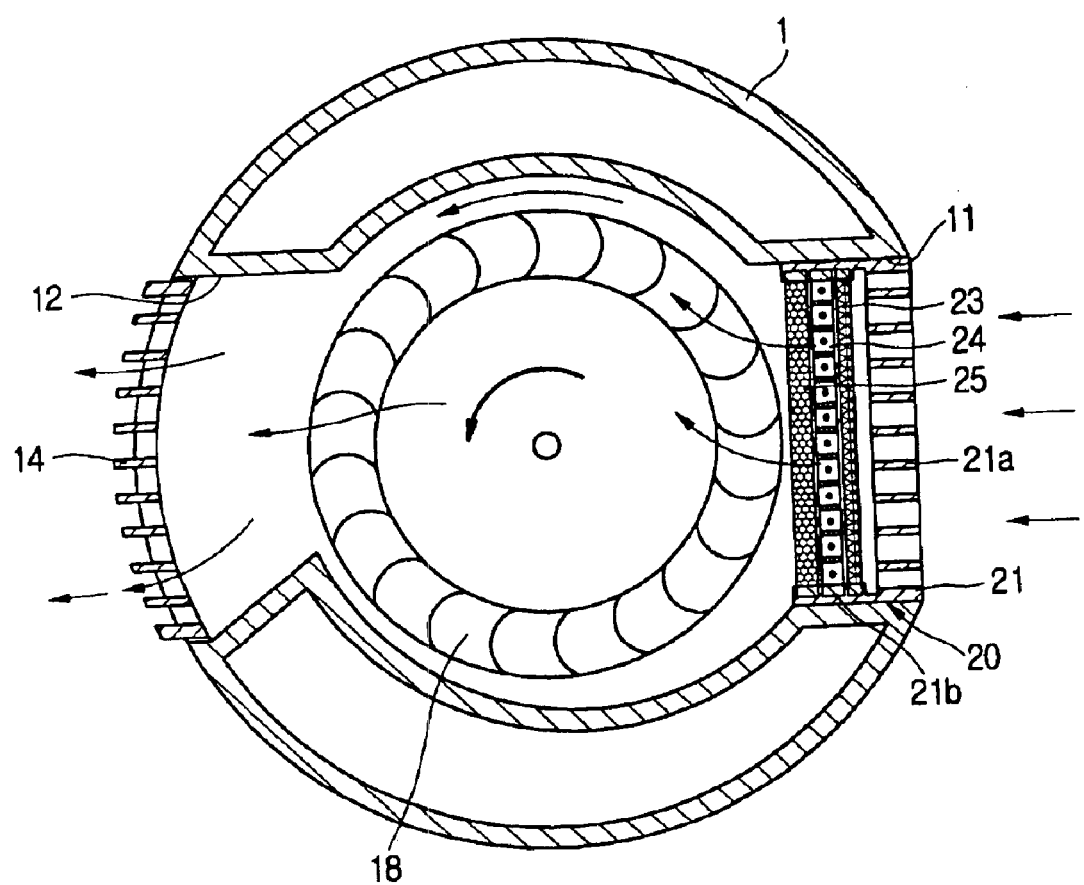
FIG. 3 is a sectional view taken along the line III–III' of FIG. 2.

As illustrated in FIGS. 1 through 3, an air cleaning apparatus according to an embodiment of the present invention includes a cabinet 1. A first air cleaning unit 10 has a cylindrical shape, and is provided on an upper portion of the cabinet 1. A second air cleaning unit 30 has a cylindrical shape like the first air cleaning unit 10, and is provided on a lower portion of the cabinet 1 to be integrated with the first air cleaning unit 10. The first air cleaning unit 10 is provided with a blowing unit 16 and a filtering unit 20, while the second air cleaning unit 30 is also provided with a blowing unit 36 and a filtering unit 40, so that the first and second air cleaning units 10 and 30 are independently operated to clean room air.

A disc-shaped support base 2 is provided on a bottom of the cabinet 1 including the two air cleaning units 10 and 30 to support the cabinet 1 so that the cabinet 1 stands upright and is stable. The support base 2 has an outer diameter larger than that of the cabinet 1. A control panel 3 is mounted on a top of the cabinet 1, and is provided with a plurality of control buttons 3a to control an operation of the air cleaning apparatus and a display 3b to display an operating state of the air cleaning apparatus. Although not shown in detail, a control unit including a circuit board and a power supply unit is provided inside the control panel 3.

A first sensor 5 is mounted to the upper portion of the cabinet 1 to sense an air pollution level of an upper part of a room, and a second sensor 6 is mounted to the lower portion of the cabinet 1 to sense an air pollution level of a lower part of the room. The first and second sensors 5 and 6 sense air pollution levels of the upper and lower parts of the room, respectively, and inform a user which part of the room has a higher air pollution level. According to data obtained from the first and second sensors 5 and 6, the first and second air cleaning units 10 and 30 are simultaneously or individually operated.

Air inlet ports 11 and 31 are provided at the cabinet 1 at positions to correspond to back sides of the first and second air cleaning units 10 and 30, respectively. Air outlet ports 12 and 32 are provided at the cabinet 1 at positions to correspond to front sides of the first and second air cleaning units 10 and 30, respectively. The air inlet ports 11 and 12 communicate with the corresponding air outlet ports 12 and 32 through a space defined in the cabinet 1. The blowing units 16 and 36 are installed at centers in the air cleaning units 10 and 30, respectively. The filtering units 20 and 40 are mounted to the air inlet ports 11 and 31, respectively. Air discharging grills 14 and 34 are mounted to the air outlet ports 12 and 32, respectively, to guide air.

The blowing unit 16 includes a cross-flow blowing fan 18 and a motor 17, and the blowing unit 36 includes a cross-flow blowing fan 38 and a motor 37. The blowing fans 18 and 38 are rotatably installed in the first and second air cleaning units 10 and 30, respectively, to be arranged upright in a vertical direction. The motors 17 and 37 are installed at lower portions of the first and second air cleaning units 10 and 30 to drive the blowing fans 18 and 38, respectively. Preferably, the motors 17 and 37 to drive the blowing fans 18 and 38, respectively, include variable speed motors which are controllable via a rotating speed thereof through an inverter control method. The motors 17 and 37 control the operation of the first and second cleaning units 10 and 30, so that the blowing fan 18 of the first cleaning unit 10 is operated at a speed higher than the blowing fan 38 of the second air cleaning unit 30, or the blowing fan 38 is operated at a speed higher than the blowing fan 18, according to the pollution levels of the upper and lower parts of the room.

The filtering units 20 and 40 have a size to correspond to the air inlet ports 11 and 31, respectively, and are removably mounted to the air inlet ports 11 and 31, respectively. The filtering unit 20 includes a filter casing 21 provided with an air sucking grill 21a, and a plurality of filters removably mounted to the filter casing 21. The filtering unit 40 includes a filter casing 41 provided with an air sucking grill 41a, and a plurality of filters removably mounted to the filter casing 41. In this case, the filter casings 21 and 41 are provided with filter support walls 21b and 41b, respectively, to support the filters which are arranged to be superposed. The filters include an antibacterial free filter 23 or 43, an electrostatic dust filter 24 or 44, and a fine dust filter 25 or 45. The antibacterial free filter 23 or 43, electrostatic dust filter 24 or 44, and the fine dust filter 25 or 45 are sequentially arranged. In this case, the antibacterial free filter 23 or 43 has a net structure with large meshes to filter relatively large dust particles. The electrostatic dust filter 24 or 44 includes a plurality of ground electrodes and discharging lines which are arranged in parallel to each other to collect dust by ionization of dust particles. The fine dust filter 25 or 45 is made of polypropylene resin or polyethylene resin to have a shape of a non-woven fabric, and functions to collect fine dust.

Thus, when room air is circulated by the operation of the blowing fan 16 or 36, the air is cleaned while passing through the filters 23, 24, and 25, or 43, 44, and 45. When a user desires to remove the filtering unit 20 or 40 from the corresponding air cleaning unit 10 or 30 so as to clean the filtering unit 20 or 40 or replace the filters 23, 24, and 25, or 43, 44, and 45, the user has only to pull the filter casing 21 or 41 out from the air cleaning unit 10 or 30, thus allowing the filters 23, 24, and 25 or 43, 44, and 45 to be easily cleaned or replaced with new filters.

The operation of the air cleaning apparatus according to the present invention will be described below.

When the air cleaning apparatus is operated using the control panel 3 provided on the top of the cabinet 1, air pollution levels are sensed by the first and second sensors 5 and 6 which are mounted to the upper and lower portions of the cabinet 1, respectively.

The control unit compares the air pollution level of the upper part of the room with that of the lower part of the room, based on the data obtained from the sensors 5 and 6. When it is determined that the air pollution level of the lower part is higher than that of the upper part, the blowing fan 38 of the second air cleaning unit 30 is individually operated, or the blowing fan 38 is operated at a speed which is higher than the blowing fan 18 of the first air cleaning unit 10, so that the air of the lower part of the room is mainly cleaned.

On the contrary, when the air pollution level of the upper part is higher than that of the lower part, the blowing fan 18 of the first air cleaning unit 10 is individually operated, or the blowing fan 18 is operated at a speed which is higher than the blowing fan 38 of the second air cleaning unit 30, so that the air of the upper part of the room is mainly cleaned.

Further, when the air pollution level is high throughout the room, the blowing fan 18 of the first air cleaning unit 10 and the blowing fan 38 of the second air cleaning unit 30 are simultaneously operated at high speed, thus cleaning the air of the upper and lower parts of the room at the same time.

According to the sensed air pollution levels of the upper and lower parts of the room, the air cleaning units 10 and 30, which are provided at the upper and lower portions of the cabinet 1, are simultaneously operated, or either of the air cleaning units 10 and 30 is operated. Further, airflow of the first and second air cleaning units 10 and 30 is appropriately regulated by controlling the speed of the motors 17 and 37.

Figure 4:
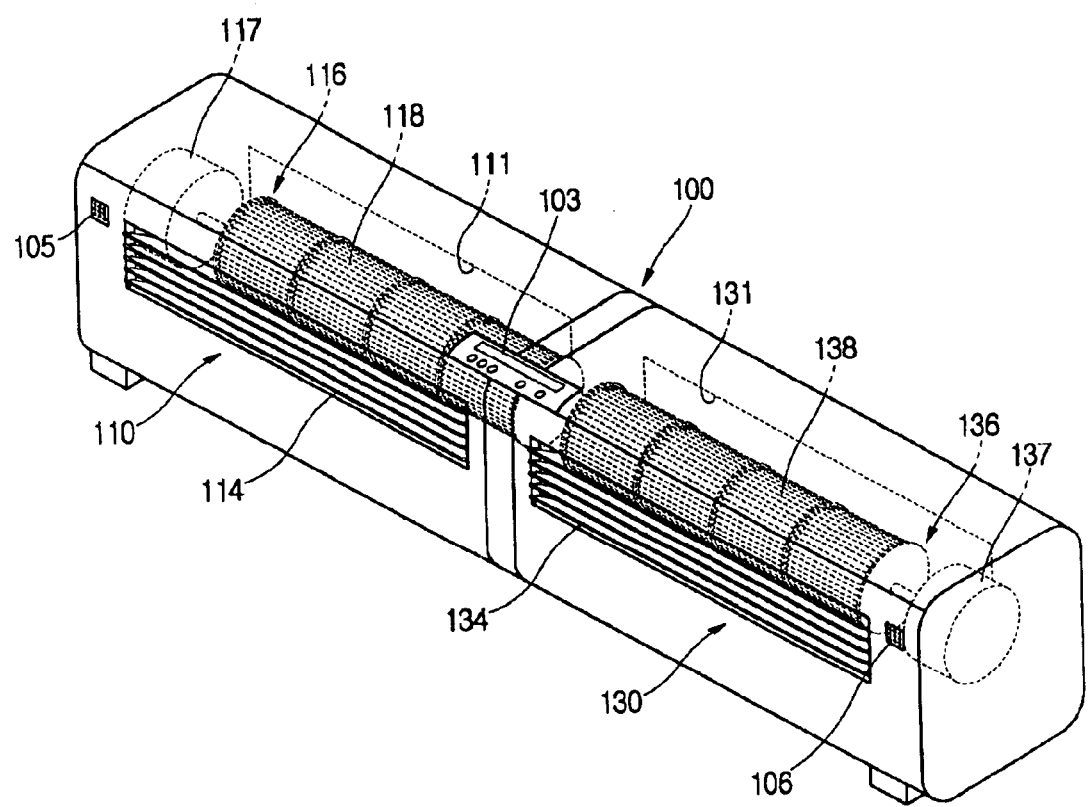
FIG. 4 is a perspective view illustrating an air cleaning apparatus, according to another embodiment of the present invention.

FIG. 4 illustrates an air cleaning apparatus, according to another embodiment of the present invention. The air cleaning apparatus includes a cabinet 100. A first air cleaning unit 110 is provided at a left side of the cabinet 100 and a second air cleaning unit 130 is provided at a right side of the cabinet 100 such that they are connected to each other. The first air cleaning unit 110 is provided with a blowing unit 116 and a filtering unit (not shown), and the second air cleaning unit 130 is provided with a blowing unit 136 and a filtering unit (not shown), so that the first and second air cleaning units 110 and 130 independently perform an air cleaning process. The blowing units 116 and 136 each are provided with a blowing fan 118 or 138 and a motor 117 or 137. Air inlet ports 111 and 131 are provided in back of the first and second air cleaning units 110 and 130, respectively. Air outlet ports 114 and 134 are provided in front of the first and second air cleaning units 110 and 130, respectively.

Further, according to the air cleaning apparatus shown in FIG. 4, a control panel 103 is mounted to a top of the cabinet 100 to control an operation of the air cleaning apparatus. A first sensor 105 is mounted to a left end of the cabinet 100 to sense an air pollution level of a left side of a room, and a second sensor 106 is mounted to a right end of the cabinet 100 to sense an air pollution level of a right side of the room. The air cleaning apparatus allows the air pollution levels of opposite sides of the room to be independently sensed by the first and second sensors 105 and 106, thus informing the user as to which part of the room has a higher air pollution level. Based on the sensed air pollution levels, the first and second air cleaning units 110 and 130 are simultaneously operated, or either of the first and second air cleaning units 110 and 130 is operated. Since the air cleaning apparatus shown in FIG. 4 is the same as the air cleaning apparatus shown in FIGS. 1 through 3, except for the above-mentioned construction and operation, the air cleaning apparatus of FIG. 4 is not described herein in detail.

As apparent from the above description, the present invention provides an air cleaning apparatus, which senses air pollution levels at opposite sides of a room by first and second sensors, and is controlled such that two air cleaning units are simultaneously operated or either of the air cleaning units is operated according to the sensed air pollution levels. The air cleaning apparatus controls speed of motors of blowing units included in the air cleaning apparatus such that airflow of the first and second air cleaning units is appropriately regulated, thus allowing room air to be effectively and uniformly cleaned in a short period of time.

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An air cleaning apparatus, comprising:
   a cabinet provided with first and second air cleaning units, said first and second air cleaning units being connected to each other and each being provided with a blowing unit and a filtering unit;
   first and second sensors provided on the cabinet to be spaced apart from each other and to sense air pollution levels at opposite sides of a room;
   a control unit to control the first and second air cleaning units so that both the first and second air cleaning units are operated, or either of the first and second air cleaning units is operated, according to data obtained from the first and second sensors.

2. The air cleaning apparatus according to claim 1, wherein said air cleaning units each are provided with an air inlet port and an air outlet port so that air is circulated through the air cleaning units, said blowing unit is installed in each of the air cleaning units, and said filtering unit is removably mounted to the air inlet port of each of the air cleaning units.

3. The air cleaning apparatus according to claim 2, wherein said blowing unit comprises:
   a blowing fan installed in each of the air cleaning units; and
   a motor installed in each of the air cleaning units to rotate the blowing fan.

4. The air cleaning apparatus according to claim 3, wherein said motor comprises:
   a variable speed motor which is controllable via a rotating speed thereof.

5. The air cleaning apparatus according to claim 2, wherein said filtering unit comprises:
   a filter casing provided with an air sucking grill and removably mounted to the air inlet port of each of the air cleaning units; and
   at least one filter installed in the filter casing and removably mounted to the filter casing.

6. The air cleaning apparatus according to claim 5, wherein said filter, installed in the filter casing, comprises:
   an antibacterial free filter, an electrostatic dust filter, and a fine dust filter which are arranged to be superposed.

7. The air cleaning apparatus according to claim 1, further comprising:
   a control panel mounted to a predetermined portion of the cabinet, said control panel being provided with a plurality of control buttons to control an operation of the air cleaning apparatus and a display to display an operating state of the air cleaning apparatus.

8. The air cleaning apparatus according to claim 1, wherein said first and second air cleaning units are provided at upper and lower portions of the cabinet, respectively, and said first and second sensors are mounted to the upper and lower portions of the cabinet, respectively.

9. The air cleaning apparatus according to claim 1, wherein said first and second air cleaning units are provided at both sides of the cabinet, and said first and second sensors are mounted to both ends of the cabinet.

10. The air cleaning apparatus according to claim 1, further comprising:
    a disc-shaped support base provided on a bottom of the cabinet to support the cabinet, and having an outer diameter larger than an outer diameter of the cabinet.

11. The air cleaning apparatus according to claim 3, wherein the motor installed in each of the air cleaning units control an operation of the air cleaning units, so that the blowing fan of the first cleaning unit is operated at a speed higher than the blowing fan of the second cleaning unit, or so that the blowing fan of the second cleaning unit is operated at a speed higher than the blowing fan of the first cleaning unit.

12. The air cleaning apparatus according to claim 6, wherein the filter casing comprises:
    filter support walls to support the antibacterial free filter, the electrostatic dust filter, and the fine dust filter.

13. An air cleaning apparatus, comprising:

a plurality of air cleaning units connected to each other;

a sensing unit to sense room air pollution levels; and a control unit to control the air cleaning units simultaneously or individually based on the sensed room air pollution levels.

14. An air cleaning apparatus, comprising:

a plurality of air cleaning units connected to each other and provided with a blowing unit and a filtering unit;

a plurality of sensors to sense room air pollution levels; and a control unit to control the air cleaning units simultaneously or individually based on data of the sensed room air pollution levels obtained by the sensors.

15. The air cleaning apparatus according to claim 14, wherein said blowing unit comprises:

a blowing fan installed in each of the air cleaning units; and a motor installed in each of the air cleaning units to rotate the blowing fan.

16. The air cleaning apparatus according to claim 15, wherein said motor comprises:

a variable speed motor which is controllable via a rotating speed thereof.

17. The air cleaning apparatus according to claim 14, wherein said filtering unit comprises:

a filter casing removably mounted to each of the air cleaning units; and a plurality of filters installed in the filter casing and arranged to be superimposed.

* * * * *